US00PP18889P2

(12) United States Plant Patent
Davis

(10) Patent No.: US PP18,889 P2
(45) Date of Patent: Jun. 3, 2008

(54) ***COREOPSIS* PLANT NAMED 'RUM PUNCH'**

(50) Latin Name: ***Coreopsis* spp.**
Varietal Denomination: Run Punch

(76) Inventor: Richard Davis, P.O. Box. 116, Locustville, VA (US) 23404

( * ) Notice: Subject to any disclaimer, the term of this patent is extended or adjusted under 35 U.S.C. 154(b) by 27 days.

(21) Appl. No.: 11/488,815

(22) Filed: Jul. 17, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—Klarquist Sparkman, LLP

(57) ABSTRACT

A new and distinct *Coreopsis* plant named 'Rum Punch' characterized by very free flowering orangey-rose daisy-like flowers, a low mounding habit and excellent vigor.

1 Drawing Sheet

Botanical designation: *Coreopsis* spp. (of unknown origin).
Variety denomination: 'Rum Punch'.

BACKGROUND OF THE INVENTION

The present invention relates to a new and distinct plant of *Coreopsis* and given the cultivar name 'Rum Punch'. *Coreopsis* is in the family Asteraceae. This new cultivar originated as a chance seedling in a container nursery garden.

SUMMARY OF THE INVENTION

The following traits have been repeatedly observed and are determined to be the unique characteristics of 'Rum Punch'. These characteristics in combination distinguish 'Rum Punch' as a new and distinct cultivar:

1. Unique orangey-rose daisy-like flowers.
2. Low, mounding habit.
3. Very free flowering.
4. Excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one year old *Coreopsis* 'Rum Punch' growing in the ground in the field in August in Canby, Oreg.

DETAILED PLANT DESCRIPTION

The following is a detailed description of the new *Coreopsis* cultivar based on observations of a one-year-old specimen grown in the ground in full sun under typical outdoor conditions in the trial fields in August in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial, grown as an annual.
- *Hardiness.*—USDA Zone 9-10.
- *Size.*—58 cm wide and 45 cm tall to top of flowers.
- *Form.*—Low mound with freely branching stems.
- *Vigor.*—Excellent.
- *Roots.*—Fibrous, freely branching, fine, and Yellow White 158A; roots develop easily from stem cuttings.

Stem:
- *Type.*—Ascending.
- *Size.*—42 cm tall and 1 to 2.5 mm wide.
- *Internode length.*—3.5 to 6.6 cm.
- *Surface.*—Glabrous.
- *Color.*—Green 137A.

Leaf:
- *Type.*—Simple.
- *Shape.*—Ternate with lobes linear, terminal lobe the longest.
- *Arrangement.*—Opposite.
- *Size.*—Grows to 9 cm long where petiole grows to 17 mm long.
- *Width.*—Grows to 8 cm wide with lobes 1 mm to 4 mm wide.
- *Margins.*—Entire.
- *Apex.*—Acute.
- *Base.*—Cuneate.
- *Surface texture.*—Glabrous.
- *Venation.*—Pinnate.
- *Color.*—Top side — Green 137A. Bottom — Green 138A.

Immature inflorescence: Globular, 5 mm wide and 5 mm deep, Greyed Purple 187B on top with a band on Greyed Yellow 161A in the middle and the bottom Yellow Green 147B.

Inflorescence:
- *Type.*—Long stalked terminal heads of daisy type flowers.

*Peduncle.*—Grows to 8.5 cm tall and 0.5 wide, glabrous, Green 137A.

*Size.*—3.5 cm wide and 10 mm deep.

*Ray florets.*—8 in number, no pistil or stamen, obovate, the tip three lobed with the terminal lobe the longest, margins entire, base cuneate, 20 mm long and 8 mm wide, glabrous on both surfaces, petals cup up, 1 mm claw at base. Color: Ray flower, topside — Greyed Purple 187C on the end half of the ray florets blending over a yellow tone closest to Greyed Orange 167C, claw Yellow 12A. Ray, bottom side — Greyed Red 182C.

*Cone.*—Conic in shape, grows to 6 mm wide and 3 mm deep, Greyed Purple 187A.

*Disc florets.*—Corolla — 4 mm long and 1 mm wide, tubular, 4 lobed, Greyed Purple 187A on the top ⅓ to Yellow Orange 14A on bottom ⅔, glabrous. Pistil — 5 mm long, 2-branched stigma extruding from the corolla, style 3.5 mm long, Orange 24A overall, ovary 1.5 mm long, White 155A. Stamen — 4, filaments 3 mm long, extruding, Black 202A, pollen Orange 24A.

*Bloom period.*—June through September in Canby, Oreg.

*Fragrance.*—Light, daisy like.

Seed: None produced.

*Fertility.*—Infertile.

Disease and pests: *Coreopsis* are susceptible to mildew and fungal spots. None of these have been observed on plants grown under commercial conditions in Canby, Oreg.

I claim:

1. A new and distinct *Coreopsis* plant as herein illustrated and described.

* * * * *

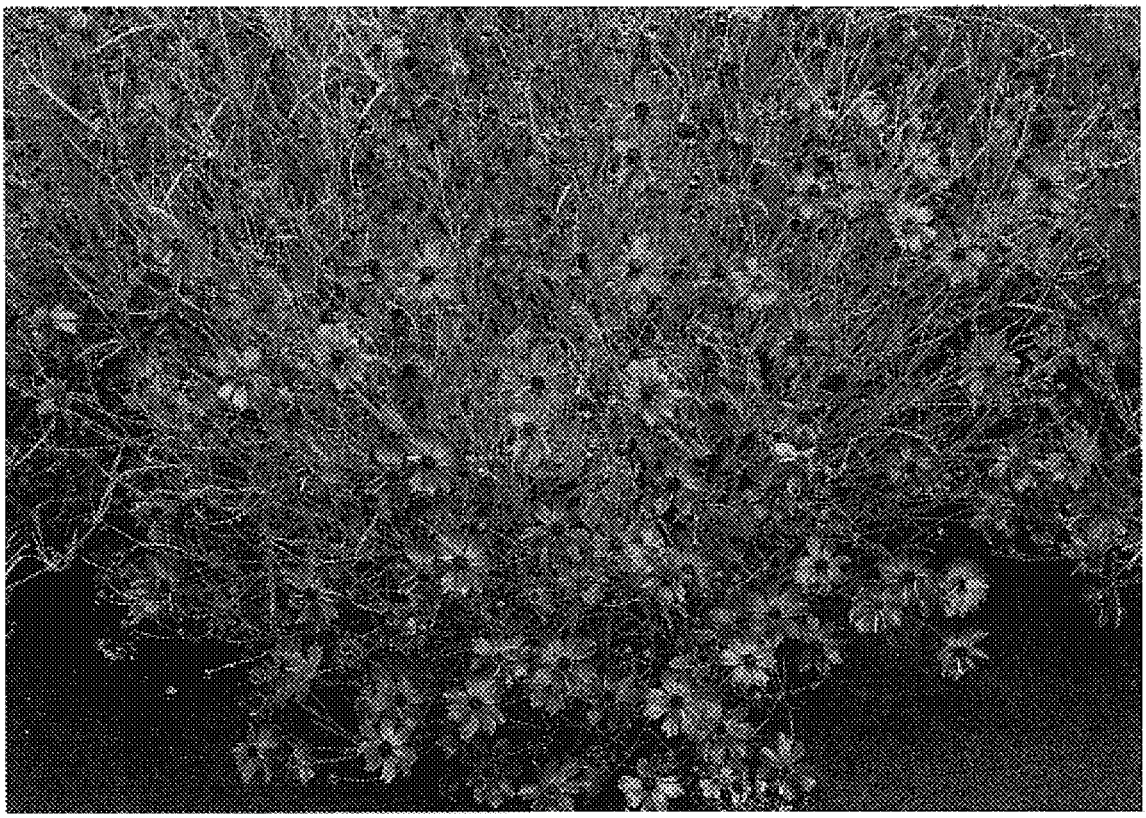

UNITED STATES PATENT AND TRADEMARK OFFICE

CERTIFICATE OF CORRECTION

PATENT NO. : PP 18,889 P2
APPLICATION NO. : 11/488815
DATED : June 3, 2008
INVENTOR(S) : Richard Davis It is certified that error appears in the above-identified patent and that said Letters Patent is hereby corrected as shown below:

On the Title Page
Item (50), Varietal Denomination, "Run Punch" should be --Rum Punch--.

Column 3, line 1, "0.5 wide" should be --0.5 mm wide--.

Signed and Sealed this

Second Day of December, 2008

JON W. DUDAS
*Director of the United States Patent and Trademark Office*